US008945473B2

United States Patent
Roberson et al.

(10) Patent No.: US 8,945,473 B2
(45) Date of Patent: Feb. 3, 2015

(54) CHEMOCHROMIC DETECTOR FOR SENSING GAS LEAKAGE AND PROCESS FOR PRODUCING THE SAME

(75) Inventors: Luke B. Roberson, Titusville, FL (US); Janine E. Captain, Titusville, FL (US); Martha K. Williams, Titusville, FL (US); LaNetra Clayton Tate, Oviedo, FL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 13/615,850

(22) Filed: Sep. 14, 2012

(65) Prior Publication Data

US 2013/0004372 A1    Jan. 3, 2013

Related U.S. Application Data

(62) Division of application No. 11/935,545, filed on Nov. 6, 2007, now Pat. No. 8,293,178.

(51) Int. Cl.
*D01F 1/04* (2006.01)
*D01F 1/10* (2006.01)
*G01N 21/78* (2006.01)

(52) U.S. Cl.
CPC .. *D01F 1/04* (2013.01); *D01F 1/10* (2013.01); *G01N 21/783* (2013.01)
USPC ............................................. 422/94; 422/86

(58) Field of Classification Search
CPC ................................ D01F 1/04; G01N 21/783
USPC ......................................................... 422/86, 94
See application file for complete search history.

(56) References Cited

U.S. PATENT DOCUMENTS

| | | | |
|---|---|---|---|
| 4,472,353 A * | 9/1984 | Moore | 422/401 |
| 4,822,743 A * | 4/1989 | Wegrzyn | 436/3 |
| 5,398,153 A | 3/1995 | Clough et al. | |
| 5,593,459 A * | 1/1997 | Gamblin | 8/539 |
| 5,849,073 A | 12/1998 | Sakamoto et al. | |
| 6,015,715 A | 1/2000 | Kirschner et al. | |
| 6,172,120 B1 | 1/2001 | Smith et al. | |
| 6,895,805 B2 | 5/2005 | Hoagland | |
| 7,253,002 B2 | 8/2007 | Marganski et al. | |
| 7,384,988 B2 | 6/2008 | Gauthier et al. | |
| 2005/0095938 A1* | 5/2005 | Rosenberger et al. | 442/194 |
| 2007/0125153 A1 | 6/2007 | Visel et al. | |
| 2007/0224081 A1 | 9/2007 | Bokerman et al. | |

* cited by examiner

*Primary Examiner* — Paul Hyun
(74) *Attorney, Agent, or Firm* — Michelle L. Ford; Jennifer P. Yancy

(57) ABSTRACT

A chemochromic sensor for detecting a combustible gas, such as hydrogen, includes a chemochromic pigment and a textile polymer. The textile material includes a chemochromic pigment operably responsive to a combustible gas. The combustible gas sensing textile material can be made by melt spinning, solution spinning, or other similar techniques. In a preferred embodiment carbon nanotubes are used with the textile material which will increase the material strength and alter the thermal and/or electrical properties. These textiles woven into fabrics can provide garments not only with hydrogen sensing capabilities but the carbon nanotubes will allow for a range of sensing capabilities to be embedded (i.e. gas, health, and electronic monitors) within the garments.

14 Claims, 4 Drawing Sheets

CHEMOCHROMIC DETECTOR FOR SENSING GAS LEAKAGE AND PROCESS FOR PRODUCING THE SAME

CROSS REFERENCE TO RELATED APPLICATION

This application claims priority under 35 U.S.C. §120 as a divisional of U.S. Utility patent application Ser. No. 11/935,545, filed Nov. 6, 2007, which issued as U.S. Pat. No. 8,293,178 on Oct. 23, 2012, the contents of which are incorporated herein by reference.

ORIGIN OF THE INVENTION

The invention described herein was made by employees of the United States Government and may be manufactured and used by or for the Government of the United States of America for governmental purposes without the payment of any royalties thereon or therefor.

TECHNICAL FIELD OF THE INVENTION

The invention relates generally to a chemochromic detector that indicates the presence of a combustible gas, such as a reducing gas, preferably hydrogen.

BACKGROUND OF THE INVENTION

Advances in fuel cells, interest in environmentally friendly vehicles, and national dependence on foreign oil have brought hydrogen ($H_2$) fuel to the forefront of the various energy candidates to meet our future energy demands. However, there remains a general perception about the safety with respect to the widespread use of hydrogen as a fuel. Hydrogen is becoming an increasingly important fuel source as conventional fossil fuel sources continue to be depleted. Hydrogen gas is colorless and without smell; therefore, possible hydrogen leaks are difficult to monitor and may go undetected. Hydrogen is a gas having the highest molecular kinetic velocity and the highest diffusibility, which makes it very susceptible of leaking. When hydrogen mixes with oxygen from air, a vigorous explosive reaction can occur and cause destruction of property and loss of life.

Known hydrogen sensors can be dangerous and difficult to use, are susceptible to interferences, and typically require a dedicated operator to control the instrumentation. It would be significant to provide an unattended, chemochromic sensor capable of detecting and providing a response in the presence of a hydrogen leak.

Another significant problem with existing hydrogen gas sensor technology is that the technology does not work in certain environments, such as in atmospheres of inert gas or at lower or variable temperatures, such as those disclosed in U.S. Pat. Nos. 5,849,073 and 6,895,805 hereby incorporated by reference.

Thus, there is a need in the art for a hydrogen detector that can overcome the above-described problems.

SUMMARY OF THE INVENTION

The invention described herein provides a chemochromic detector that indicates the presence of a combustible gas. Preferably, the combustible gas is a reducing gas. Most preferably, the combustible gas is any gas such as hydrogen, carbon monoxide, acetylene, methane, and the like. The chemochromic detector provides an indication of the presence of the combustible gas without the necessity of power consumption.

The chemochromic detector is a robust detector for indicating the presence of a gas, such as hydrogen gas, and can be readily modified for a wide variety of applications and environmental conditions. The chemochromic detector can be used in atmospheres of inert gas, hydrogen gas, or mixtures of gases, or in environments that have variable temperature, including high temperatures such as above 100° C. and low temperatures such as below −196° C.

The chemochromic detector identifies the presence of the combustible gas and provides discrete indicia of the presence of the gas to a person in proximity to the chemochromic detector, to a person monitoring cameras or fiber optic equipment, or to a person who inspects equipment for maintenance.

The preferred chemochromic detector is simple, low cost, portable, requires no power, and is simple to apply and remove. Generally, the chemochromic detector does not require any special expertise to use and provides for an unattended, chemochromic sensor capable of detecting and providing a response in the presence of a gas leak. The detector does not require active monitoring or a power source and can be easily removed after use. In other applications, where the chemochromic detector might be incorporated into a composite structure such as in hydrogen storage vessels, the technology also allows for instrumentation monitoring and change in color could be reported with a type of digital output. Potentially, the chemochromic detector could be used as an outer layer or coating for high pressure cryogenic storage tanks to monitor possible fatigue failures in the system. In this embodiment, the chemochromic detector would form a composite layer on the surface of the storage tank.

The Space Shuttle uses cryogenic liquid hydrogen ($LH_2$) as rocket fuel. For safety, the $LH_2$ is stored a distance away from the launch pad. During fueling the $LH_2$ is pumped through a vacuum-jacketed insulated pipeline to the launch pad and eventually into the external tank. During hazardous operation such as fueling the Space Shuttle, the area is restricted, and maintenance engineers are not allowed in the vicinity during fueling or several hours afterwards until the area is declared safe. The detector described herein can be installed and left unattended during the hazardous operation. After the area has been declared safe, the detector may be inspected to determine whether leaks have occurred. This allows for effective maintenance control of the pipeline by detecting the pinpoint area/source where flanges and equipment require replacement or re-work.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

The present invention is directed to a chemochromic detector that includes a chemochromic pigment and a polymer. The chemochromic detector provides an indication of the presence of the combustible gas without the necessity of power consumption. The chemochromic detector is a robust detector for indicating the presence of a gas, such as hydrogen gas, and can be readily modified for a wide variety of applications and environmental conditions, including high temperatures such as above 873 K and low temperatures such as below 20 K, most preferably 77-373 K.

Figure 1:
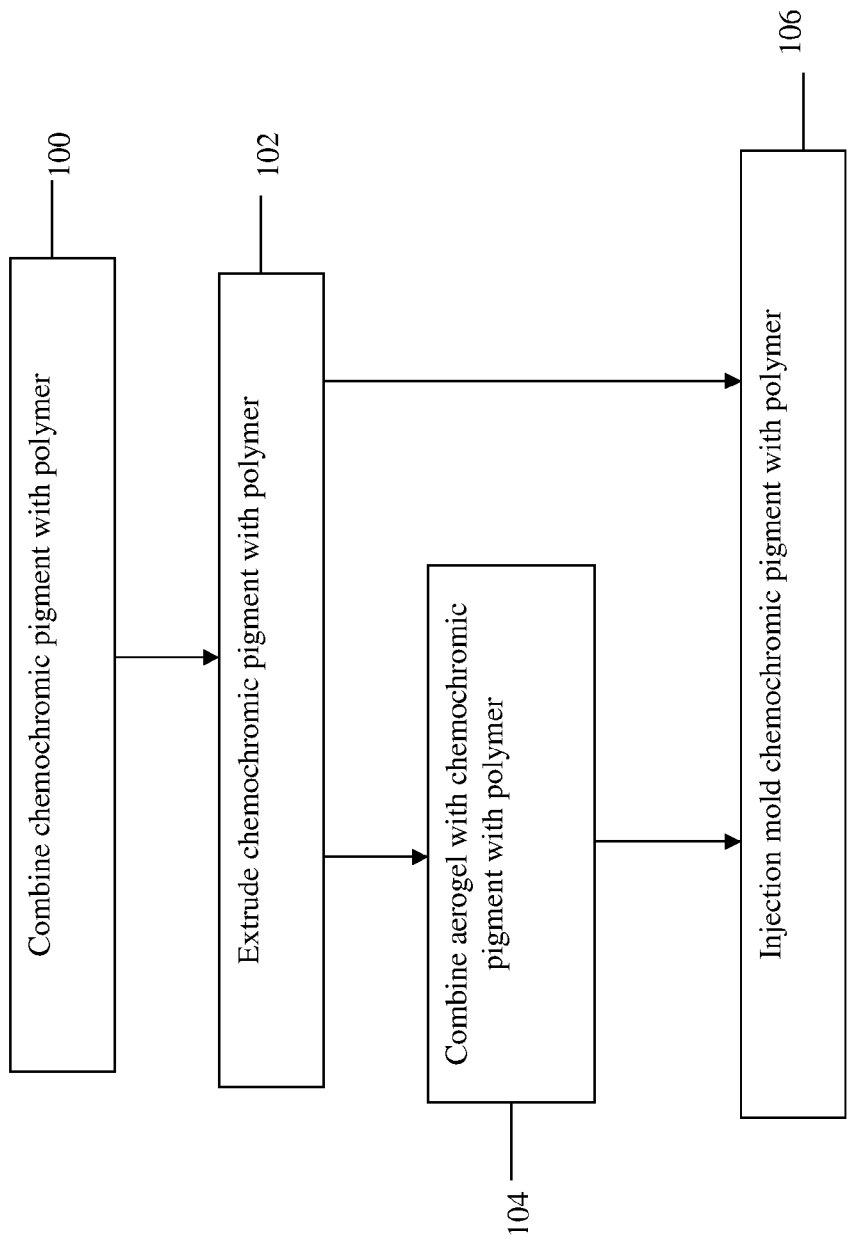
FIG. 1 illustrates a process for making a hydrogen detector according to an embodiment herein.

FIG. 1 illustrates a preferred method for making the chemochromic detector in accordance with the present invention. The method includes combining a chemochromic pigment with a polymer (100). Preferred chemochromic pigments are disclosed in U.S. Pat. No. 5,849,073 to Sakamoto and U.S. Patent Application Publication Nos. 2007/0125153 and 2007/0227081; the contents of each of these documents are expressly incorporated herein by reference. Generally, the chemochromic pigment is any pigment that is operably responsive to a combustible gas. Preferably, the operable response is a change of color upon contact with a combustible gas, such as hydrogen. The combined chemochromic pigment and polymer are then molded into a rigid or pliable shape. Preferably, the chemochromic pigment and polymer are extrusion molded, injection molded, blow molded, or fiber spun. In a preferred embodiment, the chemochromic detector is extruded into a tape, tape-like, thin-film, or formed into any shape suitable for its intended purpose.

The preferred chemochromic pigment contains particles of titanium dioxide, vanadium oxide, tungsten oxide, molybdenum oxide, yttrium oxide, or combinations thereof and at least one platinum group compound from the group of oxides, hydroxides, hydrated oxides, or combination thereof of platinum group metals deposited thereon. In another preferred embodiment, the chemochromic pigment is any pigment that includes a platinum group compound and exhibits a change of color upon exposure to a combustible gas, such as hydrogen. The chemochromic pigment preferably has a minimum color change of 0.2 ($\Delta E=0.2$) which can be measured by instrumentation. In another preferred embodiment, the chemochromic pigment has a minimum color change of 1 ($\Delta E=1$) which can be seen by the unaided eye. In still another preferred embodiment, the chemochromic pigment exhibits a color change of greater than 15 in less than 1 minute upon contact with the combustible gas. However it should be understood to one of ordinary skill in the art, that the color change can be tailored to different rates upon the loading of additional ingredients, such as aerogel. For example, aerogel inhibits gas diffusion and thereby decreases the sensitivity of the pigment and its reaction rate at room temperature. This can be very advantageous for application where parts per billion sensitivity and instantaneous leak detection are not required, but where the low thermal conductivity of the aerogel provides an advantage for thermal insulation. Gas diffusion rates of the base polymer will also play into the detection rate. For example, silicone has a fast diffusion rate, whereas polypropylene, VERSIFY, HDPE, and nylons have slower diffusion rates and different selectivity. Furthermore, polymer composite encapsulation of $H_2$ sensing pigment can allow the sensor system to be engineered to a specific application.

Platinum group metals include palladium, platinum, rhodium, and the like classified as the platinum group. Depending on the gas to be detected, a suitable platinum group compound can be selected. Oxides, hydroxides, and hydrated oxides of palladium (Pd) are preferred because of their shorter response time and higher degree of color change. Preferably, titanium dioxide ($TiO_2$) particles having an average particle size of at least 0.01 to 0.5 μm are used. $TiO_2$ provides a faster and more sensitive reaction in conjunction with a platinum group metal. Depending on the gas to be detected, a suitable substrate compound can be selected.

The chemochromic or color-changing pigment is capable of irreversibly changing from a light to a dark color when contacted by the combustible gas such as hydrogen. Upon exposure to a reducing gas, the pigments are discolored and exhibit a color change. As provided above, the color change is dependent upon a number of factors including, but not limited to, additional ingredients and polymer selected. In a preferred embodiment, the color change goes to a dark or blackish color. The color change can be detected by, but not limited to, a camera, fiber optic apparatus, electronic signal, chemical potential based on the reduction potential of the pigment, or other means known in the art.

"Polymer" shall be defined to include polymers, copolymers, and blends of polymers. Copolymers shall include all polymers having more than one monomer type, and, as such, include terpolymers, tetrapolymers, and other polymers with multiple monomer types. The polymer can be a thermoplastic polymer, including, but not limited to, acrylics, acrylonitriles, epoxy, ethylene vinyl alcohol, ethylene-vinyl acetate, fluoroplastics, liquid crystal polymers, polyacetals, polyacrylamides, polyacrylates, polyamide-imides, polyamides, polyanilines, polybutadienes, polybutylenes, polycarbonates, polydienes, polyesters, polyethers, polyethylenes, polyimides, polyketones, polynitriles, polyolefins, polypropylene, polysiloxanes, polystyrenes, polysulfones, polyurethanes, polyvinyl alcohols, polyvinylchlorides, polyvinyls, polyvinylidenes, silicone, other suitable thermoplastics, derivatives or combinations thereof. Additionally, the polymer may be made of nylons, polyether imides, thermoset polymers, derivatives, or combinations thereof. Typically, the polymer is selectively permeable to the combustible gas, such as hydrogen. Other polymers can be used depending on the gas to be selected or the intended purpose. To facilitate use and optimize performance, the polymer is preferably supplied in the form of a polymer matrix that is flexible, hydrophobic, and has reduced permeability to water vapor, oxygen, and other reducing gases. The pigment can detect precisely and conveniently the leakage of combustible gases such as hydrogen, carbon monoxide, acetylene, methane, and the like.

The color-changing pigment alone is not suitable for outdoor environments especially the harsh conditions that exist at NASA Kennedy Space Center (KSC). For the detector to function in such a harsh environment as that experienced by the $LH_2$ transfer lines, an aerogel additive is combined with the chemochromic pigment and polymer. In a preferred embodiment, the pigment is combined with aerogel and interdispersed within a polymer matrix. Aerogel is a filler material and known to have exceptionally low density and low thermal conductivity. Aerogel in powder form is readily commercially available. For example, a silica aerogel formed by a relatively low-cost process is described by Smith et al. in U.S. Pat. No. 6,172,120, hereby incorporated by reference. Aerogels are available in both hydrophilic and hydrophobic forms. Hydrophilic aerogels typically have a higher thermal conductivity and may be less useful for certain thermal and/or electrical insulation applications due to water adsorption. Hydrophobic aerogel materials have excellent water repellency, which makes them suitable for many thermal insulation applications. The addition of 1-15% aerogel thermally insulates the color-changing pigment. Addition of the aerogel increases the rate and magnitude of color change during exposure at cryogenic conditions. As previously stated, the color change, also referred to as dE or ΔE, can be tailored to different rates (ΔE vs. time) depending on loadings levels of the aerogel, which provides a lower reaction rate at non-cryogenic temperatures. This can be very advantageous for applications where ppb sensitivity and instantaneous leak detection are not necessary. The choice of polymer matrix and gas diffusion rates of the base polymer will also play into the rate of detection.

The detection system still responds to hydrogen after exposure to highly acidic environments, such as those exposed to launch conditions at KSC.

Because gaseous hydrogen is flammable, certain applications require the detector to be free of static charge, a potential ignition source if a discharge to ground occurs. Thus electrostatically dissipative (ESD) additives can be incorporated into the detector to prevent static charge accumulation. ESD additives can be incorporated at loading levels between 0.1 and 40 weight percent. ESD additives can be organic or inorganic by chemical composition and include but are not limited to antistatic agents (i.e. LAROSTAT, ATMER, CHEMSTAT, TEGIN, PATIONIC, PELESTAT, and J STAT), inherently conductive particles, metal nanoparticles, inherently conductive polymers, and carbon nanotubes.

As previously indicated, the detector can be injection molded or fiber spun into desired shapes or designs. Creating the detector in these forms makes for a simple, low cost, ready to use, portable detector. In these forms, the detector can be used by someone with little expertise and provides for an unattended, chemochromic sensor capable of detecting and providing a response in the presence of a hydrogen leak. Fabricating the detector into these forms allows for variation in the overall size of the detector. The detector can be made into nearly any width and length, allowing a customized fit. The versatility of the forms allows the detector to be cut to the desired size in the field, enabling technicians to customize the detector 'on the spot' for intended operations. Furthermore, the detector becomes possible to package in simple kits with varying types, widths, or lengths enabling the end user to handle most applications encountered. In addition to the versatility, the detector is extremely robust because the polymer matrix is durable, flexible, pliable, and can conform to the shape of the area suspected of hydrogen leakage. In certain applications the polymer is rigid and is custom made for application geometry.

In an embodiment, an additive can further be added to enhance performance or detection at ambient temperatures and lower temperatures. The additive can be a salt, a polyelectrolyte, an ionic or non-ionic surfactant, carbon nanotubes, or combinations thereof. Since the reaction of the chemochromic pigment is based on a redox reaction, additives can alter the reactivity of the system by modifying the pigments response time to the gas. Some additives may be added that hinder the chain movement and result in a higher Tg than a neat form, The additive can be conductive, such as carbon nanotubes (both single walled and multi walled), which exhibit promising gas sensing properties due to their high surface area, geometry, and electronic transport properties. The nanotubes can be functionalized with platinum or palladium. This surface modification will not only enhance the physical interaction between the pigment and the carbon nanotubes but will enhance the hydrogen sensing capabilities of the carbon nanotubes. Sayago et al. (MRS Proc. 2006) found that surface modification with palladium increased the nanotubes sensitivity to hydrogen. Kumar et al. (J. Phys. Chem 2006) stated that carbon nanotubes functionalized with platinum exhibited good hydrogen sensing responses at room temperature. Oakley et al. (Nanotechnology 2005) found that palladium coated single walled carbon nanotubes were effective at sensing hydrogen at room temperature while only using ~0.25 mW power. Cusano et al. (Applied Physics Letters 2006) showed hydrogen sensing capabilities of single walled nanotubes at cryogenic temperatures. The use of carbon nanotubes in the sensor system (with and without other additives like aerogel) detailed in this document can result in a detector that can be tuned to detect hydrogen at lower levels without the consumption of power. Incorporation of carbon nanotubes is expected to have positive benefits that would be application specific.

The detector can also have an adhesive layer attached to at least a portion of a surface to aid in attaching the detector to a surface. The adhesive can be peelably or removably affixed to a disposable material such that when the disposable material is removed the adhesive remains on the detector.

In another embodiment, the invention provides for combustible gas sensing textile material including a chemochromic pigment and a textile polymer. The textile material includes a chemochromic pigment operably responsive to a combustible gas, such as hydrogen. The pigment may be combined, as provided above, with at least one composition of carbon nanotubes, aerogel, polymer, salt, polyelectrolyte, graphite, or combinations thereof. The chemochromic pigment contains at least one of titanium dioxide, vanadium oxide, tungsten oxide, molybdenum oxide, yttrium oxide, or combinations thereof and at least one compound of oxides, hydroxides, hydrated oxides, or combination thereof of platinum group metals. The chemochromic pigment exhibits a color change as provided above. In the preferred embodiment, the color change is greater than 15 in less than 1 minute upon contact with hydrogen gas.

The textile polymer can be acrylics, acrylonitriles, epoxy, ethylene vinyl alcohol, ethylene-vinyl acetate, fluoroplastics, liquid crystal polymers, polyacetals, polyacrylamides, polyacrylates, polyamide-imide, polyamides, polyanilines, polybutadienes, polybutylenes, polycarbonates, polydienes, polyesters, polyethers, polyethylenes, polyimides, polyketones, polynitriles, polyolefins, polypropylene, polysiloxanes, polystyrenes, polysulfones, polyurethanes, polyvinyl alcohols, polyvinylchlorides, polyvinyls, polyviylidenes, silicones, other suitable thermoplastics, derivatives or combinations thereof.

The combustible gas sensing textile material can be made by melt spinning, solution spinning, or other similar techniques. A non-woven fabric, a mat, or felt may be the desired form of the textile material. A non-woven fabric, mat, or felt can be made using techniques as melt blowing and spun bonding methods, or any other means of making non-woven matted fabrics. Because these spinning techniques produce very small fibers, they can impart high surface area and porosity to textile.

In another embodiment, non-matted fibers may be the desired form, which can be used to make other forms, such as, but not limited to, woven cloth, braids, knits, and other arrangements of fibers desired for the particular end use application. A fiber can be made by any known means of making fibers. Examples of techniques for making fibers include, but are not limited to, melt spinning, electro-spinning, gel spinning, wet spinning, dry spinning, and dry-jet wet spinning. Similar to the techniques for making non-woven fabrics, mats, and felts, these fiber spinning techniques can also impart high surface area and porosity to the resulting textile.

After the desired form is made, the remaining solvent, if any, is removed. Any known means for removing the solvent may be used. Examples of means for removing solvent, include, but are not limited to, vacuum drying, ambient evaporation, heating, coagulation in a non-solvent, or combinations thereof. After removing the solvent, if any, the form, such as a film, can, optionally, be cut into pieces of the shape suitable for the desired end use application.

Utilizing aerogel with the textile material will improve thermal and/or electrical insulation applications. In addition, using carbon nanotubes with the textile material will increase the material strength and alter the thermal and/or electrical properties. These textiles woven into fabrics can provide garments not only with hydrogen sensing capabilities but the carbon nanotubes will allow for a range of sensing capabilities to be embedded (i.e. gas, health, and electronic monitors) in the garments. Additionally, incorporation of nanoparticles into polymer fibers using solution and dry fiber spinning techniques can improve the properties of the base polymer matrix.

Example 2 illustrates a method for detecting hydrogen gas. The method includes preparing a detector comprising a chemochromic pigment operably responsive to hydrogen combined with an additive selected from carbon nanotubes, aerogel, polymer, or combinations thereof. The chemochromic pigment contains titanium dioxide, vanadium oxide, tungsten oxide, molybdenum oxide, yttrium oxide, or combinations thereof and at least one compound selected from oxides, hydroxides, hydrated oxides, or combination thereof of platinum group metals. The detector exhibits a color change of greater than 1 ($\Delta E > 1$) upon contact with hydrogen gas. The detector is attached at a location to be tested and then detects a color change.

The response to color change was measured using a Konica Minolta Chromameter, CR400. The difference between two colors is expressed in $\Delta E$, where a $\Delta E$ value of zero represents a perfect match. The greater the $\Delta E$ value, the poorer the match and the more responsive the detector. A $\Delta E$ of 1.0 is perceivable visually, while an electronically measured $\Delta E$ less than or equal to 0.2 represents the best match obtainable for commercial products.

Figure 2:
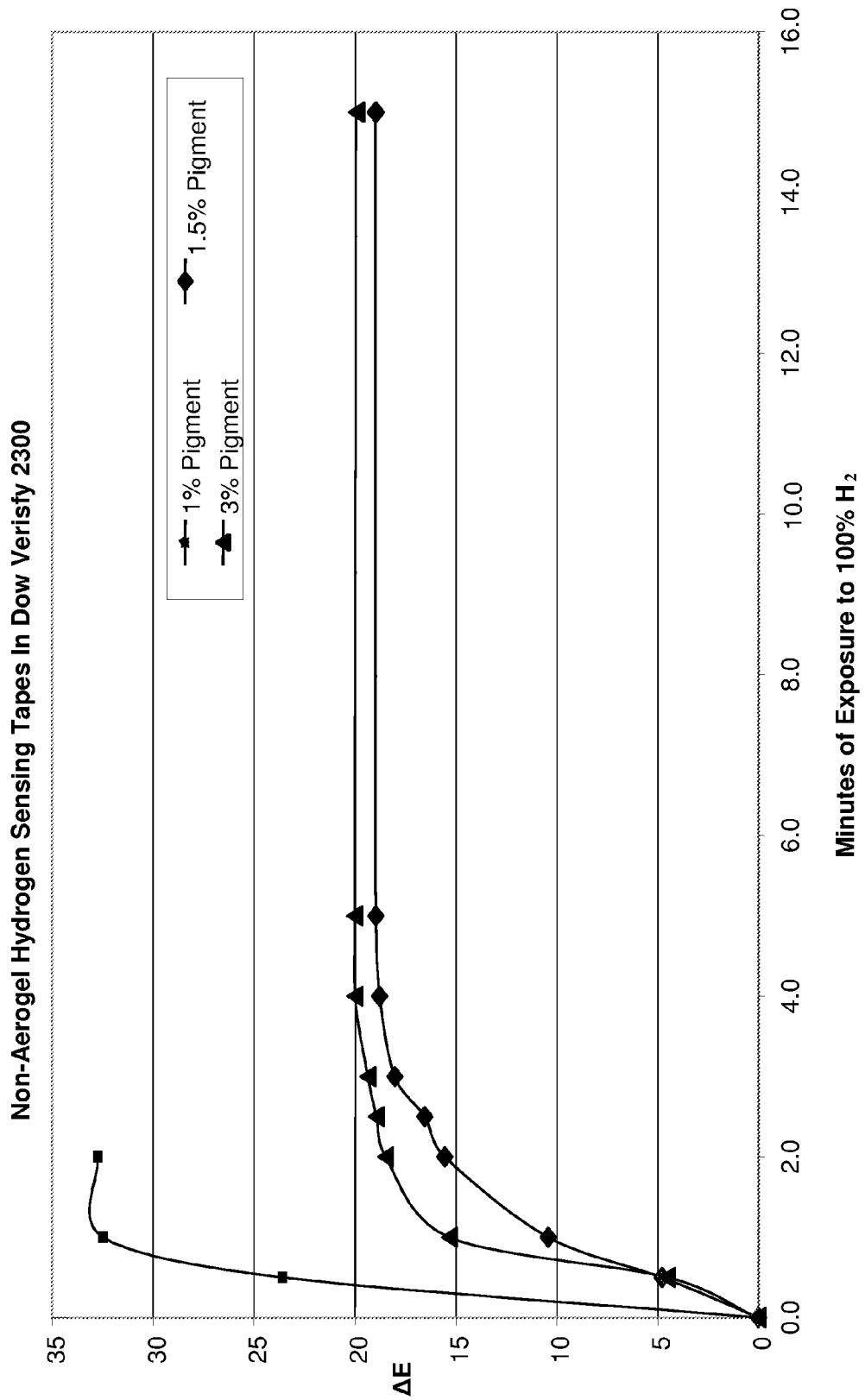
FIG. 2. graphically shows the response to hydrogen (delta E) of different loading levels of composite hydrogen detecting sensors.
Figure 3:
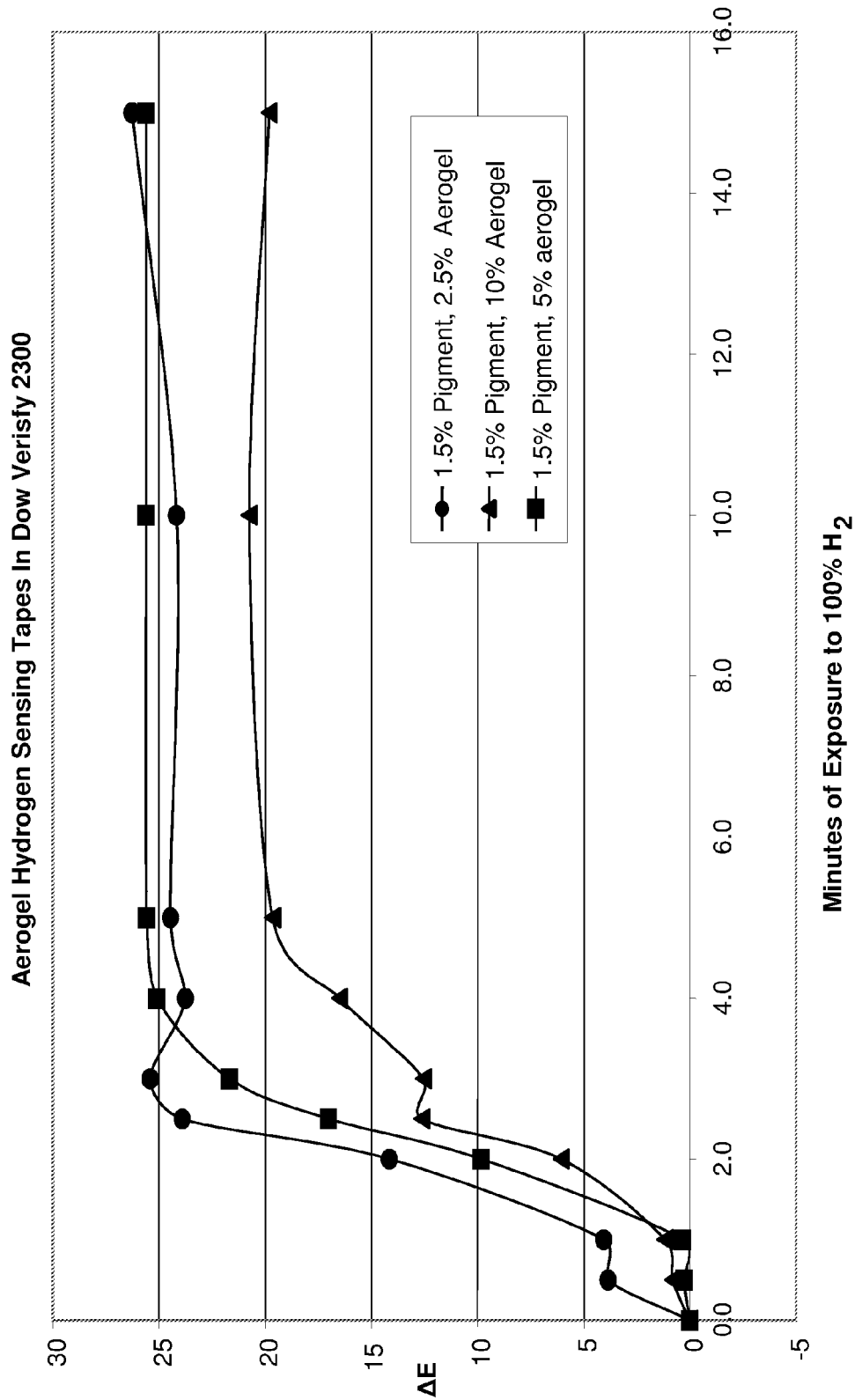
FIG. 3. graphically displays the composite sensor's response to hydrogen (delta E) for VERSIFY containing aerogel composites at different concentrations.
Figure 4:
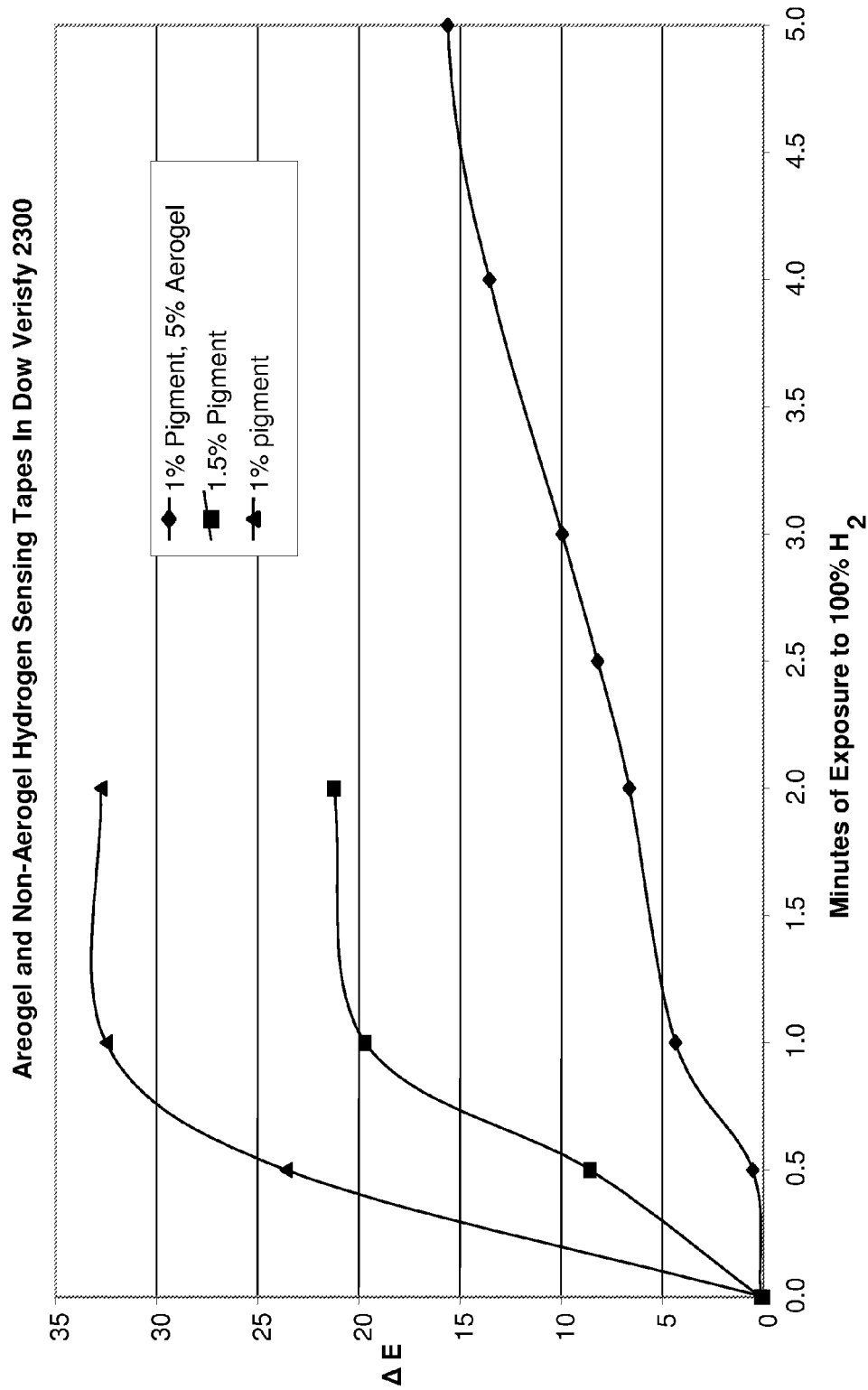
FIG. 4. graphically shows the cryogenic response to hydrogen (delta E) of different hydrogen detecting sensors with and without aerogel.

FIGS. 2-4 are graphs showing a color change in response to hydrogen for different sensors. Although FIGS. 2-4 illustrate different embodiments of the invention and demonstrate its advantages, it is understood that they do not restrict this invention.

FIG. 2 shows the color change response ($\Delta E$) for different levels of hydrogen pigment loadings over time. The amount of color change decreases with the addition of pigment. Aerogel containing composites are able to decrease the response time which is desirable in particular applications.

FIG. 3 is a graph showing the color change response for different levels of aerogel loadings at 1.5% pigment concentration. Large $\Delta E$ values are observed at all loading levels of aerogel at room temperature. Novel composites are able to slow down response which is desirable in particular applications. The response time can be tailored based on percent loading.

FIG. 4 is a graph showing the observed response in color change between aerogel and non-aerogel extruded tapes. The addition of aerogel decreases the rate of color change at room temperature. This means that the sensitivity can be tailored based on the aerogel concentration, which may be advantageous for certain applications. Exposure at cryogenic temperatures with aerogel increases the sensitivity of the pigment, which may be advantageous for some applications.

The following examples illustrate different embodiments of the invention and demonstrate its advantages; they do not restrict this invention.

EXAMPLES

Example 1

Preparation of the Hydrogen Detector without Aerogel 1.5 weight percent hydrogen sensing pigment was dry mixed with 98.5 weight percent base polymer material, i.e. Dow VERSIFY 2300. The dry mixture was extruded using a counter-rotating Brabender twin screw extruder at zone temperatures of 185, 190, 195 and a die temperature of 200° C. The die was either a 2-inch or 6-inch ribbon die for tape extrusion. Screw speeds of 35 and 60 rpms were used for the 2-inch and 6-inch dies respectively. Draw of the ribbon reduced the width of the tapes to 1.5 and 4.5 inches. Tape thicknesses were kept between 0.5 and 0.7 mm.

Example 2

Preparation of the Hydrogen Detector with Aerogel 3.0 g hydrogen sensing pigment was dry mixed with 10.0 g Aspen Aerogel and 187 g of base polymer material, i.e. Dow VERSIFY. The dry mixture was extruded using a counter-rotating Brabender twin screw extruder at zone temperatures of 190, 195, 195 and a die temperature of 200° C. The die was either a 2-inch or 6-inch ribbon die for tape extrusion. Screw speeds of 35 and 60 rpms were used for the 2-inch and 6-inch dies respectively. Draw of the ribbon reduced the width of the tapes to 1.5 and 4.5 inches. Tape thicknesses were kept between 0.5 and 0.7 mm.

Example 3

Preparation of the Hydrogen Detector with/without Aerogel and Injection Molding 1.5 weight percent hydrogen sensing pigment was dry mixed with 98.5 weight percent base polymer material, i.e. Dow VERSIFY. The dry mixture was extruded using a counter-rotating Brabender Mark II twin-screw extruder at zone temperatures of 190, 195, 195 and a die temperature of 200° C. A ⅛" diameter rod die was used at a screw speed of 60 RPM to form a composite rod. The rod was hand-drawn through a water bath and dried. The rod was then pelletized using a Cumberland pelletizer. Composite pellets were then fed into a Nissei NEX50-5E injection molding machine. The 5 zone temperatures were set to 200° C. and mold temperature at 90° C. Parts were fabricated between 0.25 and 0.02 inches thick using a variety of stainless steel molds. For aerogel samples, 1.5 weight percent pigment was added to 5 weight percent aerogel and 93.5 weight percent polymer.

Additional advantages, features, and modifications will readily occur to those skilled in the art. Therefore, the invention in its broader aspects is not limited to the specific details and embodiments shown and described herein. Accordingly, various modifications may be made without departing from the spirit or scope of the general inventive concept as defined by the appended claims and their equivalents.

We claim:
1. A combustible gas sensing garment comprising
   a chemochromic pigment interdispersed within a textile polymer, wherein said chemochromic pigment is combined with aerogel or xerogel, said chemochromic pigment is operably responsive to a combustible gas and said textile polymer is provided in the form of fibers that are woven to provide said garment.

2. The garment of claim 1, wherein said chemochromic pigment is selected from the group consisting of titanium dioxide, vanadium oxide, tungsten oxide, molybdenum oxide, yttrium oxide, and combinations thereof and at least one compound selected from the group consisting of oxides, hydroxides, hydrated oxides, and combination thereof of platinum group metals deposited thereon.

3. The garment of claim 1, wherein said polymer is selected from the group consisting of acrylics, acrylonitriles, epoxy, ethylene vinyl alcohol, ethylene-vinyl acetate, fluoroplastics, liquid crystal polymers, polyacetals, polyacrylamides, polyacrylates, polyamide-imide, polyamides, polyanilines, polybutadienes, polybutylenes, polycarbonates, polydienes, polyesters, polyethers, polyethylenes, polyimides, polyketones, polynitriles, polyolefins, polysiloxanes, polystyrenes, polysulfones, polyurethanes, polyvinyl alcohols, polyvinylchlorides, polyvinyls, polyvinylidene, silicones, thermoplastics, thermoset polymers, derivatives and combinations thereof.

4. The garment of claim 1, wherein said chemochromic pigment is combined with at least one electrostatically dissipative additive.

5. A method of making the garment of claim 1, comprising fiber spinning said chemochromic pigment with aerogel or xerogel.

6. The method of claim 5, further comprising fiber spinning said chemochromic pigment with an additive selected from the group consisting of an electrostatically dissipative additive, a salt, a polyelectrolyte, an ionic or non-ionic surfactant, carbon nanotubes, and combinations thereof.

7. The garment of claim 1, wherein said chemochromic pigment is combined with carbon nanotubes.

8. The garment of claim 1, wherein said chemochromic pigment is combined with at least one polyelectrolyte.

9. The garment of claim 1, wherein said chemochromic pigment is combined with at least one ionic or non-ionic surfactant.

10. The garment of claim 1, whereby said fibers are formed by melt spinning or solution spinning.

11. The garment of claim 1, whereby said fibers are formed by a technique selected from electro-spinning, gel spinning, wet spinning, dry spinning and dry-jet wet spinning.

12. The garment of claim 1, wherein said combustible gas is selected from hydrogen, carbon monoxide, acetylene and methane.

13. The garment of claim 12, wherein said combustible gas is hydrogen.

14. The garment of claim 12, wherein said chemochromic pigment is operably responsive to a combustible gas without the necessity of power consumption.

* * * * *